(12) United States Patent
Levinson

(10) Patent No.: US 6,398,729 B1
(45) Date of Patent: Jun. 4, 2002

(54) DYSMETRIC DYSLEXIA SCREENING PROCEDURE ADMINISTERED ON THE INTERNET

(76) Inventor: Harold N. Levinson, 15 Lake Rd., Great Neck, NY (US) 11020

( * ) Notice: Subject to any disclaimer, the term of this patent is extended or adjusted under 35 U.S.C. 154(b) by 0 days.

(21) Appl. No.: 09/442,471

(22) Filed: Nov. 18, 1999

(51) Int. Cl.⁷ .................................................. A61B 5/00
(52) U.S. Cl. ...................................................... 600/300
(58) Field of Search ................................. 600/300, 559, 600/558; 434/116, 350; 351/239, 223

(56) References Cited

U.S. PATENT DOCUMENTS

| | | | | |
|---|---|---|---|---|
| 3,842,822 A | * | 10/1974 | Levinson et al. | 600/300 |
| 3,952,728 A | * | 4/1976 | Levinson et al. | 600/300 |
| 6,035,328 A | * | 3/2000 | Soukal | 600/300 |
| 6,045,515 A | * | 4/2000 | Lawton | 600/558 |
| 6,213,956 B1 | * | 4/2001 | Lawton | 600/558 |

* cited by examiner

*Primary Examiner*—Kevin Shaver
*Assistant Examiner*—Brian Szmal
(74) *Attorney, Agent, or Firm*—Myron Amer P.C.

(57) ABSTRACT

For a dysmetric dyslexia-identifying test herebefore administered to a mixed audience of children, some being dyslexic and others not, the administration thereof now over the Internet to a dispersed audience preferably consisting of a child in the singular in facing relation to an Internet display module, to thereby obviate by this dispersion any audience-influencing behavior which heretofore affected the test results.

1 Claim, 3 Drawing Sheets

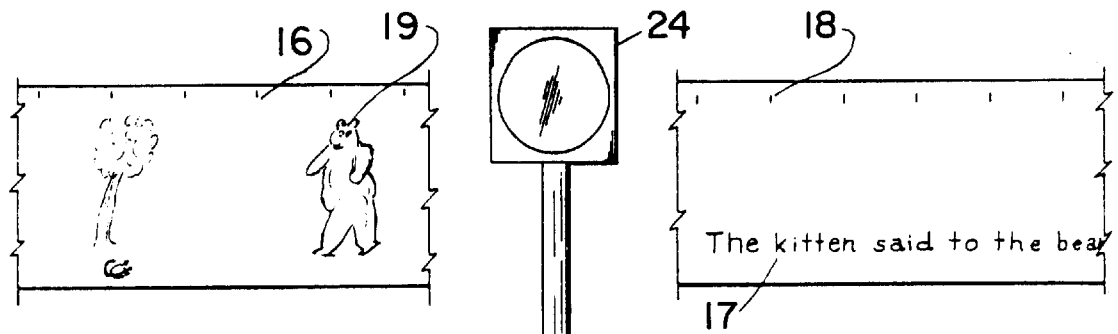
FIG. 4a PRIOR ART
FIG. 4b PRIOR ART
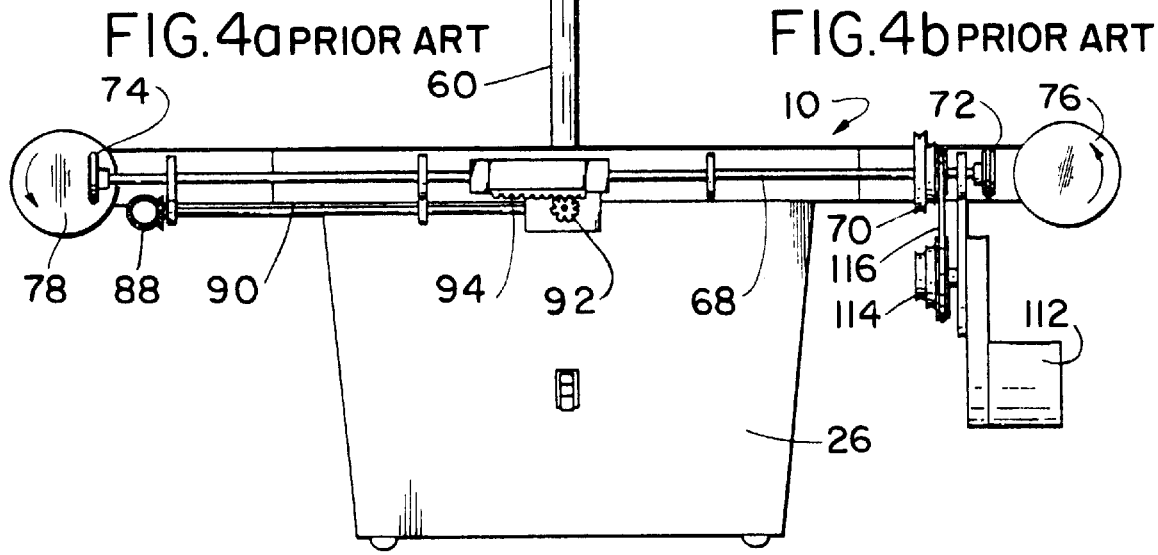
FIG. 3 PRIOR ART
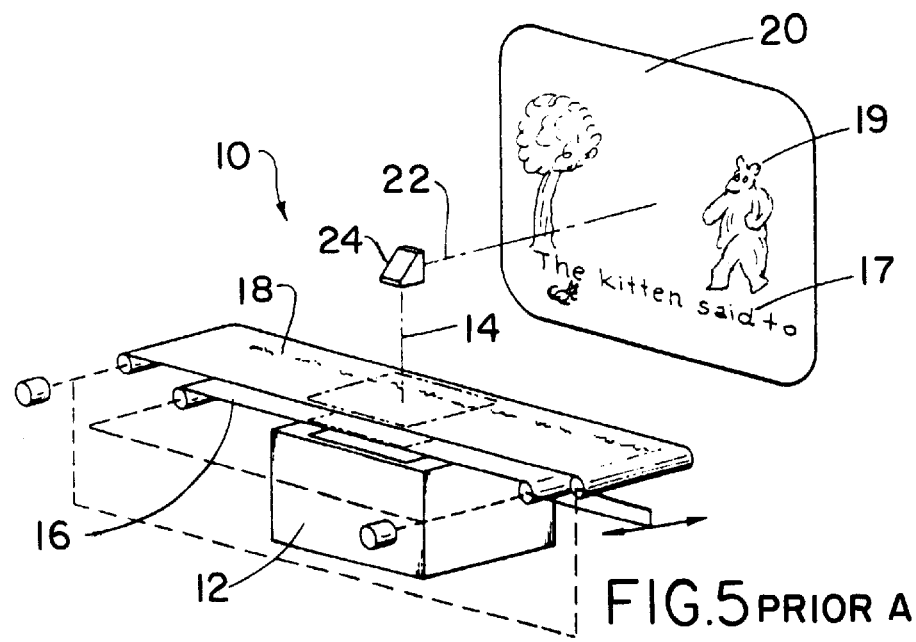
FIG. 5 PRIOR ART

DYSMETRIC DYSLEXIA SCREENING PROCEDURE ADMINISTERED ON THE INTERNET

The present invention relates generally to improvements in a known diagnostic screening procedure implemented by administering a reading or symbol-recognition test that effectively identifies children, even of pre-school age, as having cerebellar-vestibular dysfunctions and, in medical parlance, being affected with dysmetric dyslexia wherein the improvements, more particularly, retain the substantive validity of the test and are in the nature of the administration of the test to the end of contributing significantly to the accuracy of the test, as will be better understood as the description proceeds.

EXAMPLE OF THE PRIOR ART

It is already known, as set forth in U.S. Pat. No. 3,842,822 for "Dysmetric Dyslexia Screening Procedure", issued to Harold N. Levinson on Oct. 22, 1974, of the discoveries involving children, some possibly dysmetric dyslexic and others not, of an eye oscillation of a selected extent which is normally below the level which produces blurred vision in those children not affected with dysmetric dyslexia but, in those children affected with dysmetric dyslexia, the noted eye oscillation in response to a reading or symbol-recognition exercise is increased to a higher extent which produces blurred vision, while the non-susceptible children continue to read without reporting any blurring.

To take full advantage of the benefits of the noted discoveries, it was administered heretofore to a classroom-filled audience since to the audience, it was like watching a movie and thus was a pleasant activity well known to each participant. The test results to a significant extent correlated with the conditions of those affected with dysmetric dyslexia and those not so affected but, in practice, there was noted a variation in successive testing of a child participant, the cause of which was not understood.

Broadly, it is an object of the present invention to continue achieving the benefits of the noted diagnostic screening procedure but without any variation or other shortcomings of the prior art.

More particularly, it is an object of the invention to obviate audience-influencing behavior which has now been diagnosed as the cause of the noted variation, and thus achieve a more accurate correlation between test results and those children who are and who are not afflicted with dysmetric dyslexia.

The above brief description, as well as further objects, features and advantages of the present invention, will be more fully appreciated by reference to the following detailed description of a presently preferred, but nonetheless illustrative embodiment of an apparatus for practicing the methods of the present invention, when taken in conjunction with the accompanying drawings, wherein:

FIG. 3 is a side elevational view of the apparatus showing still further structural features;

FIGS. 4a and 4b are related illustrations respectively showing the background and foreground of the visual display utilized in practicing the known procedures and methods hereof;

Figure 6:
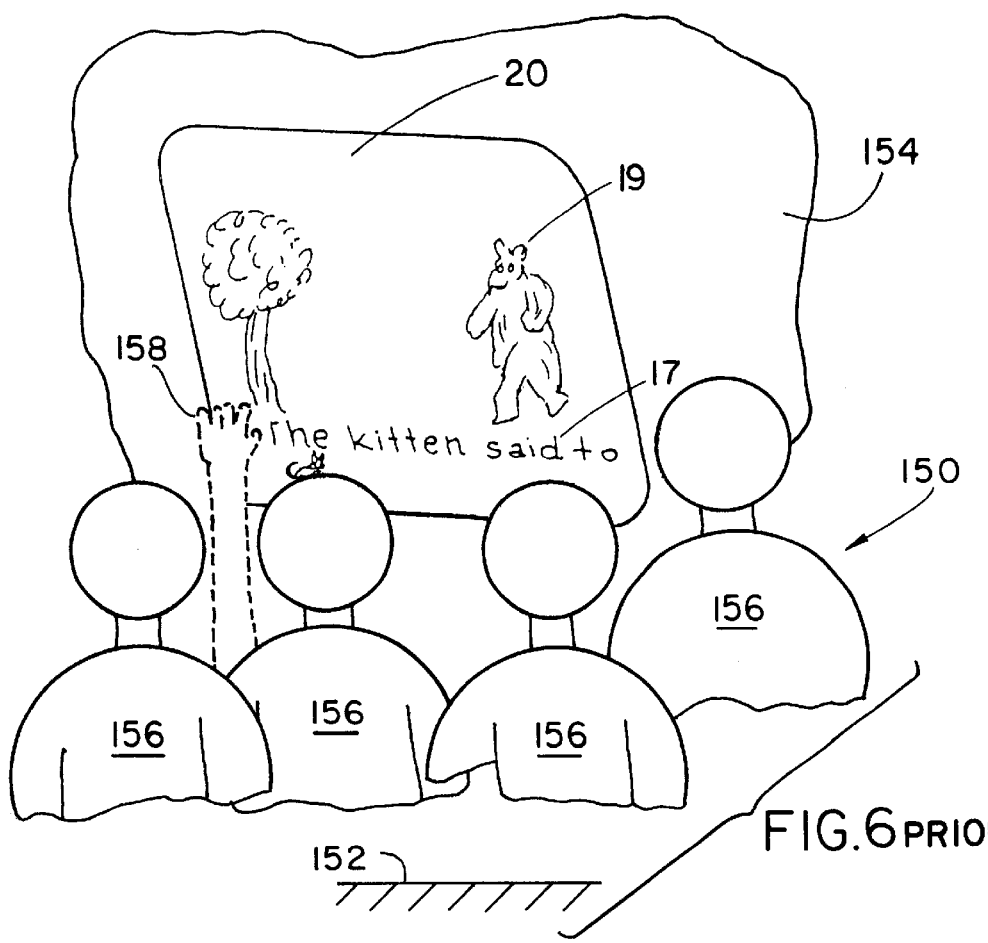
Figure 7:
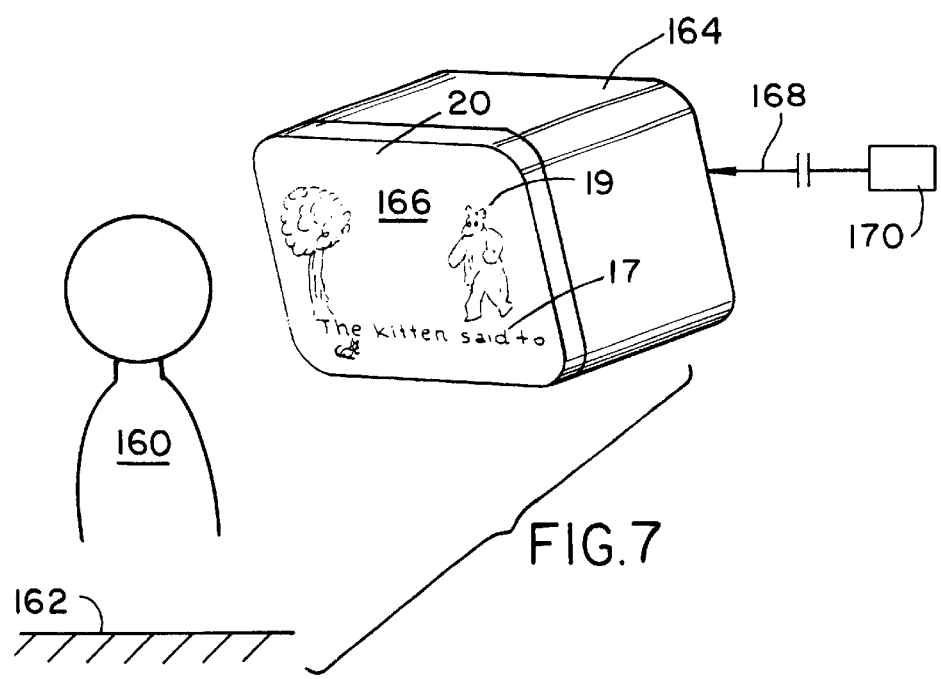

FIG. 5 diagrammatically illustrates how said foreground and background are superimposed and used in the practice of the known diagnostic screening procedures and methods;

FIG. 6 is a view from the rear of an audience participating in the known diagnostic screening method as administered in accordance with the prior art, and illustrating in phantom perspective a hand signal of one of the participants; and FIG. 7 is a side elevational view of the administration of the known diagnostic screening method as administrated in accordance with the present invention on the Internet.

THE DYSMETIC DYSLEXIA SCREENING TEST

AS ADMINISTERED BY THE APPARATUS OF

U.S. Pat. No. 3,842,822 OF FIGS. 1–6

The inventive methods and procedures of the present invention are, in essence, practical ways of implementing and using a basic discovery which has been made of children afflicted with a cerebellar-vestibular dysfunction and resulting dysmetric dyslexia. This discovery is that such children have a nystagmus, which more specifically is a low order, involuntary, swinging or oscillating eye movement occurring on the average of one beat per second, herein referred to as a sub-clinical. Thus, with such children, at all times there is movement in their eyes occurring at said one beat per second, which interferes with the vision of these children. This abnormal eye movement is, as noted, sub-clinical in nature, in that measurement thereof requires an electronystagmographic frequency recording under favorable conditions.

The foregoing sub-clinical dysfunction or nystagmus has, in turn, been traced to the presence of a cerebellar-vestibular dysfunction which prevents ocular fixation and sequential scanning of letters and words in a proper manner. Specifically, during sequential scanning or normal reading by dysmetric dyslexic children, letters and words are disordered, and letter and word scrambling or blurring results. For example, the biggest or first letter of the word is often fixated first during the slow right-to-left phase of the nystagmus. The rapid left-to-right phase often skips over several letters of a whole word until another letter is automatically fixated and scrambling or blurring results. The patient, therefore, confuses letters and words which differ only or mainly in special placement, i.e. b=d=p=q, a=e, e=3, c=u, m=w, saw=was, no=on, etc.

While there are already known methods of detecting dysfunctioning of the cerebellar-vestibular circuits, which methods are time consuming, one such typical method being caloric stimulation of the vestibular apparatus and utilizing electrostagmographic recordings. These prior methods often result in great discomfort to the patient requiring, for example, cold and warm caloric stimulation of the patient's ear and vestibular apparatus. In sharp contrast to the foregoing, there is described herein a rather simple procedure for early detection and prediction of dysmetric dyslexia, even at age levels difficult for detection, as in pre-school and kindergarten children, In essence, one of the methods or procedures hereof includes forcing an examination group to visually track or "read" textual material or symbols during movement. This forced reading in turn induces vibration of the patient's eyes at a frequency which, in the case of normal vision, is below the threshold level of blurred or scrambled vision. However, this induced vibration, when added to the subclinical eye vibration and nystagmus of dysmetric dyslexic children produces blurred vision in what they see, while normal children can still see clearly the moving texual material or symbols. Thus, those children in the examination group who indicate that they are experiencing blurred vision automatically identify themselves as possibly being dysmetic dyslexic.

A variation of the foregoing, which constitutes a second group diagnostic screening procedure or method according to the present invention, also uses the basic discovery theretofore mentioned of sub-clinical nystagmus in dysmetic dyslexic children, but in a slightly different way. Specifically, the examination group is required to have visual fixation on a designated point which is in the foregoing of a visual display, and which display has a movable background. Thereafter, movement is imparted to the background to induce a mild nystagmus interfering with the visual fixation of those of the examination group. This interference is normally below the threshold level of normal children who can block out this interference and continue there visual fixation on the designated point. However, children afflicted with a cerebellar-vestibular dysfunction and dysmetric dyslexia, and thus having the aforementioned sub-clinical nystagmus, have difficulty maintaining their visual fixation on the designated point. In fact, the sub-clinical nystagmus results in these children losing their fixation on said designated point and instead fixating on a background point which however, as already indicated, is moving. It has been found that children afflicted with dysmetric dyslexia have difficulty controlling their vision to the extent that they can return to the task of maintaining visual fixation on the stationary designated point on the foregoing, particularly with the interference caused by the moving background. In this way also, therefore, the discovered sub-clinical nystagmus is utilized as a basis for a simple, effective diagnostic screening procedure for identifying dysmetic dyslexic children in a large examination group containing same and also children with normally functioning cerebellar-vestibular circuits.

Reference is now made to the drawings wherein there is shown an appropriate projector apparatus, generally designated 10, for practicing the screening procedures or methods of the present invention. Apparatus 10, more particularly, is the -one recommended for inducing a nystagmus or eye vibration of a selected extent which results in identification of dysmetric dyslexic children when in additive relation to the discovered sub-clinical nystagmus or eye vibration being experienced by said children. To the above end, and as is perhaps best illustrated diagrammatically in FIG. 5, apparatus 10 includes a light source 12 which is beamed, as along the path 14, through physically superimposed transparencies 16 and 18, functioning respectively as background 19 and foreground 17, so as to produce a composite visual display 20

The beamed projection along the path 22 is achieved with a conventional projector or optical element 24 which may be a prism or the like. The projected visual display 20 thus consists, in part, of foreground which, in turn, may consist of symbols or the illustrated words "the kitten said to," designated 17, which foreground is on the transparency 18 and is projected by the overhead projector 24 to a viewing position a part of the composite visual display 20. The other part of the display 20 consists of background symbols or the like, as exemplifed by the drawing of the bear, designated 19, which is set forth on the transparency 16 and similarly is projected by the overhead projector 24 into viewing position as part of the visual display 20.

The portion of the transparency 16 containing the reproductions thereon which contribute to the projected background image 19 is set forth in FIG. 4a, while the coextensive portion of the transparency 18 containing the foregoing text material 17 is set forth in FIG. 4b.

As illustrated in FIG. 5, each transparency 16 and 18 is in the specific form of an elongated strip and, as will be described in greater detail subsequently, each is operatively arranged to be independently urged through movement at selected rates of speed. This is, the projected foregoing 17 and background 19 can be moved at any selected speed, in feet per second, simultaneously, or the foregoing material 17 can be held stationary while the background material 19 is moved relative thereto, or vice versa.

Figure 1:
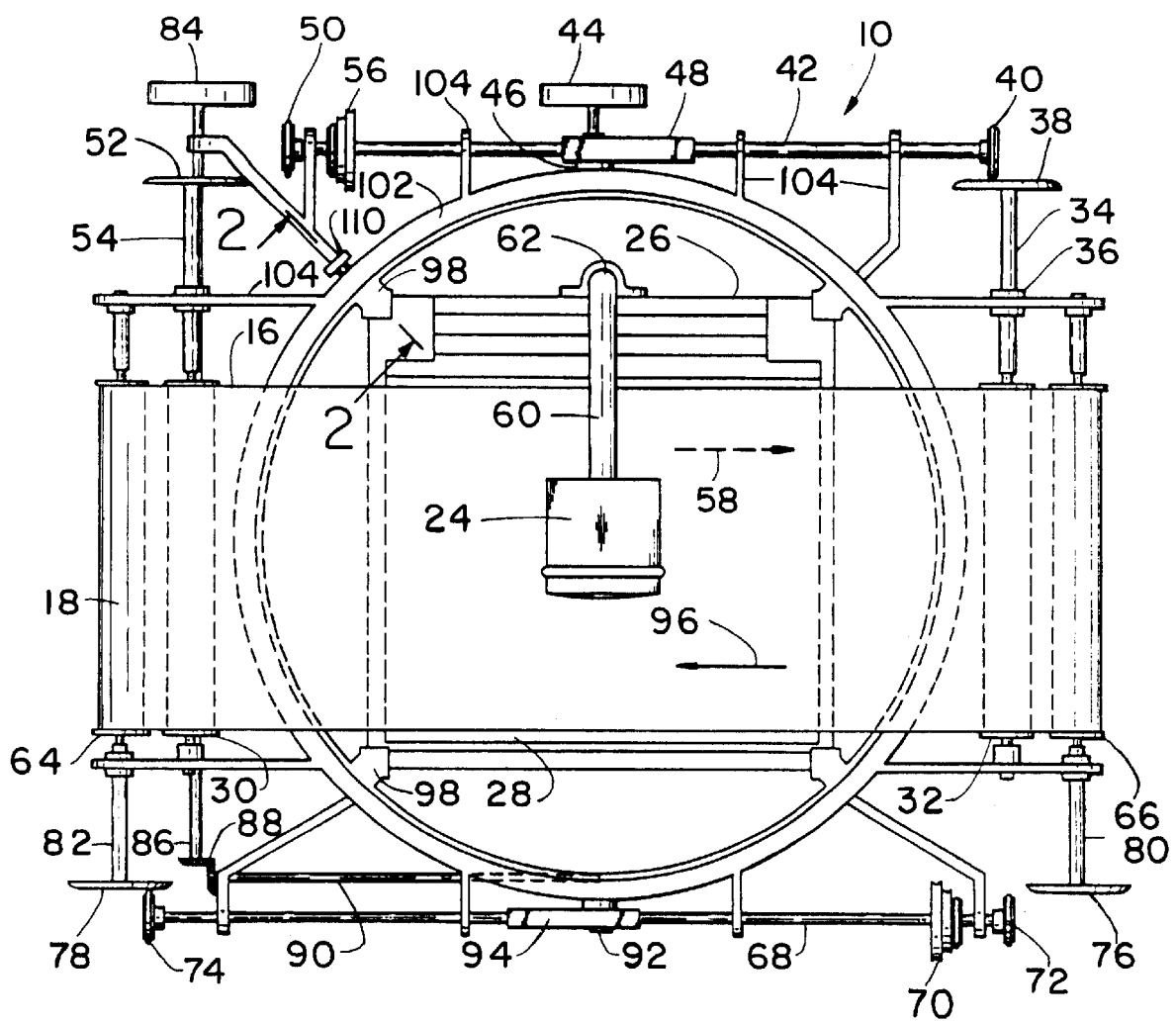
FIG. 1 is a plan view of a known apparatus for practicing the diagnostic screening procedures or methods according to the prior art.
Figure 2:
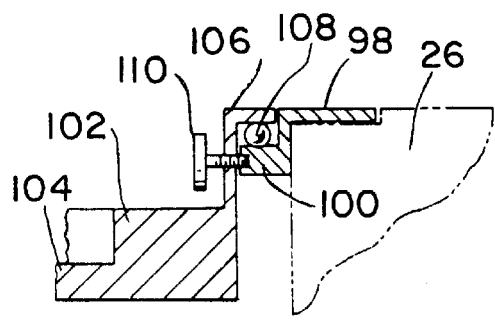
FIG. 2 is a partial side elevational view, in section taken on line 2—2 of FIG. 1, illustrating further structural features of said apparatus.

As best illustrated in FIGS. 1–3, apparatus 10 includes a housing 26 for the light source 12 and has a transparent panel 28 as its upper surface. The background transparency strip 16 is arranged to be urged through movement across panel 28, being entrained on feed roller 30 at one end and on take-up roller 32 at its opposite end. To power take-up roller 32 in rotation, there is provided a spindle extension 34 on this roller, approximately mounted in bearings, as at 36, and terminating in a driven friction disc 38. As illustrated in FIG. 1, in driving relation with disc 38 is driving disc 40 mounted on rod 42 which is shiftable in position by turning manipulation of the control knob 44 of pinion 46 in meshing engagement with rack 48. The counterpart of driving disc 40 is disc 50 mounted at the opposite end of rod 42 and shiftable into driving relation with the friction surface of driven disc 52 on the spindle extension 54 of the supply roller 30. To power the rod or drive shaft 42 in rotation, there is a step pulley 56 having a pulley drive connection to an electric motor or the like. It should be readily appreciate that not only do the driving discs 40 and 50 selectively drive the roller 32 and 30 in rotation, but by properly locating the disc 40 relative to the rotation axis of the roller 32, control can be exercised over the speed at which roller 32 rotates, and thus the speed at which the transparency strip 16 is advanced along the path 58 beneath the overhead projector 24.

In the above regard, projector 24 is arranged in proper projecting relation to the transparency 16 and also to the transparency strip 18, by being mounted on the end of an L-shaped cylindrical rod 60. Proper positioning of the projecting element 24 is achieved by pivotally mounting rod 60, as at 62, on the housing 26.

In a very similar fashion as that already described, transparency strip 18 is also operatively arranged for movement at selected speeds in projecting relation to the overhead projecting element 24. Specifically, and as illustrated, a supply length of the transparency strip 18 is supported on the supply roller 64 and is advanced therefrom, beneath the projecting element 24, and attached to the take-up roller 66. A laterally shiftable rod or drive shaft 68 is provided having a step pulley construction 70 in driving relation via pulley belt 116 and pulley 114 with an electric motor 112 (FIG. 3). Said shaft 68 has mounted at opposite ends drive discs 72 and 74. These discs are selectively moved into driving relation with driven discs 76 and 78 on extensions 80 and 82 of the take-up roller 66 and supply roller 64, respectively. Since it is convenient to have the control for the rollers 64 and 66 on the same side as control 44, the control knob 84 thereof is selected adjacent the knob 44 and has extended therefrom a rod 86 in meshing engagement, as at 88, with a further control rod 90. Rotation of rod 90 in turn causes, as best illustrated in FIG. 3, rotation in pinion 92 which is in meshing engagement with rack 94. Thus the direction of the shifting or control movement in the drive shaft 68 selects which of the driven discs 76 or 78 is to be powered in rotation. As illustrated in FIG. 1, the driving connection is made between discs 74 and 78 which produces directional movement 96 in the transparency strip 18 returning the same to the supply roller 64.

To provide additional flexibility either in the manner or in the orientation in which the component parts of the visual display are set forth in the projection being viewed by the examination group, the overhead projection 24 and the structure mounting and controlling the transparency strips 16 and 18 are rotatably mounted relative to the light source housing 26. In this respect, as illustrated in FIG. 2, mounted about the periphery of the housing 26 is a ring 98 having a lower laterally extending track 100. An outer ring-like body is mounted for rotative movement about the housing 26. Body 102 has rods connecting it to all of the previously described structures for supporting and controlling the transparency strips 16 and 18, said connecting rods being individually and collectively designated 104. The other end of body 102 has a construction providing an upper track 106. Between the tracks 100 and 106 are circumferentially spaced ball bearings 108 which enable rotational traverses in the body 102 relative to the stationary house 26. A threadible member 100 is provided to maintain any selected rotated position of ring 102 relative to the control housing 26.

The foregoing apparatus 10 is merely exemplary of a device for producing a visual display 20 that is useful in inducing or requiring reading activity in an examination group situated in viewing position before the display 20. Specifically, this reading activity consist of the members of the examination group being required to read or recognize the display materials 17, 19 while these materials are being moved at a selected rate of speed from left to right, as viewed in FIG. 5. Experimentation with the apparatus 10 has indicated that imposing this requirement on the examination group results in each member of the group experiencing an eye vibration, or back-and-forth eye movement, at a frequency or number of beats per second which is related to the feet-per-second speed of the moving visual display 20. This eye movement at said number of beats per second, when added to the sub-clinical oscillation or beats per second characteristic of dysmetric dyslexic children inflicted with a dysfunction of the cerebellar-vestibular circuit, results in blurred or scrambled vision. In this connection it is generally understood that in order to see something clearly, the eyes must fix on the object. When there is eye movement, however, or movement interfering with this visual fixation, the result is blurred or scrambled vision.

Children with normal functioning cerebellar-vistibular circuits can tolerate a certain extent of eye vibration or beats per second without complaining of blurred vision. This is what is referred to herein as the normal threshold level, i.e., the level of eye movements or beats per second at which there is clear vision, but beyond which there is blurred vision, for said referred to normal children. However, for dysmetric dyslexic children, the tolerance for eye vibrations or beats per second is much less, since such children start off with the previously referred to discovered sub-clinical eye vibration or nystagmus.

Using the apparatus 10 described herein, experiments with children of various ages have produced significant data on the blurring or scrambling speeds of normal children compared to dysmetric dyslexic children. The experiments utilized words set forth on the transparency strip 18 that had 1½ inch capital letters, ¾ inch lower case letters, and spacings of ¾ inch between letters and four inches between words, projected as said textual material 17 approximately 6 feet into display position. The younger dysmetric dyslexic children experienced blurred or scrambled visualization of the material 17 at half the running speed in the display 20 that could be tolerated by normal children of the same age. Due to compensation, a dysmetric dyslexic child soon performs as well as a normal child, experiments indicating that this typically occurs at an average age of 10 years. Highlights of the experiment are set forth in the below table.

| | Speeds at which blurring or scrambling occurs | |
|---|---|---|
| | Moving foreground 17 Fixed background 19 feet/sec | Fixed foreground 17 Moving background 19 |
| Normal children of ages 4 to 8 years | 6 to 9 | No blurring of foreground 17 |
| Dysmetric dyslexic children of ages 5 to 8½ years | 2.2 to 5 | Blurring of foreground 17 at background speeds of 4 feet/sec |

The specific values set forth above are not important and can vary, but what is important is that there is a significant difference, quantatively, in the speed at which the displayed matter 17, 19, produces blurred vision in so-called normal children, on the other hand, and in dysmetric dyslexic children on the other hand. This difference is effectively used, as explained herein, to identify dysmetric dyslexic children from normal children in a large examination group consisting of these children.

Another effective screening method according to the present invention which is. practiced using the apparatus 10 consists of the following. The examination group is required to have visual fixation on a selected portion of the foregoing material 17, such as the word "kitten." When the members of the group indicate that is has been done, for example, by appropriate hand signals, the background material 19 is then placed in motion. The moving background material 19 interferes with the ability to maintain visual fixation on the foregoing image 17 for dysmetric dyslexic children only. However, since the dysmetric dyslexic children have the aforesaid sub-clinical nystagmus, this has the unfortunate result of moving their eye focus from the target 17 to an adjacent area, which consist of the moving background or symbols 19. Experimentation has indicated that dysmetric dyslexic children have difficulty getting back onto the target material 17, while normal children have no such difficulty. Thus, those members of the examination group which indicate, again by appropriate hand signals or orally, that they cannot clearly see the designated foreground target material 17 or stay focused thereon, automatically identify themselves as possibly being dysmetric dyslexic.

From the foregoing, it should be readily appreciated that the medical discoveries disclosed herein consisting in major part of first tracing the proper or refractory response to reading instruction characteristic of dysmetric dyslexic children to a manifested dysfunction of the cerebeller-vestibular circuit, and second, a discovered sub-clinical nystagmus or eye vibration at an almost imperceptible frequency or beats per second which exist in dysmetric dyslexic children, have been carried to a further level of utility in accordance with the present invention. Specifically, these discoveries have been utilized in a noteworthy manner in the formulation, as disclosed herein, of simple, effective group diagnostic screening procedures or methods for identifying children who are possibly dysmetric dyslexic. Once identified, it is of course contemplated that these children will be further tested to confirm the existence of this condition, as for example by caloric stimulation of the vestibular apparatus. The significant point, however, is that the confirming test, which is known to be time-consuming and difficult to administer, is reserved just for this function, and an easy-to-administer screening test as described herein, and which constitutes the present invention, is effectively and advantageously used to reduce the number of members of the examination group who are to receive the confirming examination. Moreover, of presently known tests, the tests herein described have a higher degree of accuracy in identifying the existence of dysmetric dyslexia and thus even function as an improved confirming examination.

THE DYSMETRIC DYSLEXIA-SCREENING TEST AS ADMIMSTRERED OVER THE INTERNET OF FIG. 7

As previously noted, and as best understood from FIG. 6, the dyslexia-identifying test of U.S. Pat. No. 3,842,822 is one that is administered to a group 150, typically at a test site 152 located in a school during which children, usually in the age range of 4 to 8 years, are seated in facing relation to a display 20 projected on a wall 154 by a projector 10 located at the test site 152.

By previous instructions, the participants, individually and collectively designated 156, are asked to participate in the test procedure by providing a signal, such as a raising of a hand 158, when dyslexia symptoms, such as blurring of the displayed objects 17, 19 are perceived.

As evidenced by the previously noted chart setting forth "speeds at which blurring or scrambling occurs" there is significant accomplishment of dysmetic-dyslexia identification for the purposes intended. However, for convenient reference there has been set forth below and added to the chart the designation "Perceptual Instability," which it will be understood is a noted variation in successive group testing of the same children which, heretofore, was not understood.

| Speeds at which blurring or scrambling occurs | | |
| --- | --- | --- |
| | Moving foreground 17 Fixed background 19 feet/sec | Fixed foreground 17 Moving background 19 |
| Normal children of ages 4 to 8 years | 6 to 9 | No blurring of foreground 17 |
| Dysmetric dyslexic children of ages 5 to 8½ years | 2.2 to 5 | Blurring of foreground 17 at background speeds of 4 feet/sec |
| Perceptual Instability | n | % |
| Impaired Fixation, Refixation, or Background-blurring | 24 | 52.2 |
| Movement Illusions | 15 | 32.6 |

Underlying the present invention is the recognition that as to each child tested as part of a classroom audience, with an assumed imperfect understanding as to what constitutes "blurring," which the child has been instructed to report by the raising of a hand, that the implementing by the child of the instructions provided is influenced by the raising of the hand of a neighbor to cause the child to do likewise, or conversely the child may be embarrassed to be the first to raise a hand and thus does not do so when the child does experience "blurring." Also a simple inattentiveness might contribute to the noted "Perceptual instability."

To obviate audience-influencing behavior, as just generally noted, the dysmetric-dyslexic screening test is administered on the Internet which, as generally known, is an electronic network that links millions of computers together so that they can communicate with each other, including a so-called World Wide Web, which is an electronic facility that enables people to view some of the information that is available through the Internet, and is divided into individual "web sites."

Referring now to FIG. 7, the audience group 150 of the prior art is significantly reduced in number, possibly to 3 and preferably to only 1, and the child 160 selected for testing, based on reading and other cognitive difficulties as possibly being dyslexic, is seated at a test site 162 in facing relation to an Internet module 164 to respond to the visual display 20 consisting of textual materials or symbols 17, 19 or the like, urged in movement on the screen 166. The transmission 168 to the test site 162 is from a remote location 170 which, in practice, could be interstate or even international. This contributes to the utility of the administration of the dysmetric-dyslexia test over the Internet by enabling the projected display 20 of a single projector 10 at a remote location 170 to provide testing service to thousands of test sites 162.

More significant, being tested in a non-audience environment, the child 160 is not vulnerable to behavior that has heretofore resulted in "Perceptual Instability."

While the method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. In the known test to identify a reading dysfunction administered in a school environment to a classroom-filled audience of children previously instructed to provide a raised hand signal indicative of a blurred condition of a visual display observed en masse by said audience, the improvement consisting of a method contributing to a reported signal more accurately being correlated to a child's perception of the said blurred condition of the said display comprising the steps of:

(1) using a known electronic network electronically connected to operate as an internet transmitting images from at least one broadcasting site to not less than 150 sites of reception of said images;

(2) administering said known test using an observable display presented on a screen of an internet module located at each said 150 sites of reception;

(3) locating each said internet module in each of said 150 sites of reception in a selected private environment;

(4) reducing to one the child to be tested in each said private environment seated in facing relation to said internet module screen and simultaneously broadcasting images thereto so as to correspondingly simultaneously cause said administration of said test and (5) instructing each said child to use a raised hand signal when perceiving said observed display blurred;
    whereby when said child reports by said raised hand signal as instructed it is known to be uninfluenced by any reported signal of another child to thereby contribute to the accuracy of the test results of said at least 150 children simultaneously tested.

* * * * *